United States Patent
Bauer et al.

(10) Patent No.: US 12,274,772 B2
(45) Date of Patent: *Apr. 15, 2025

(54) BLEACHING COMPOSITION FOR KERATIN FIBERS

(71) Applicant: KAO CORPORATION, Tokyo (JP)

(72) Inventors: Peter Bauer, Darmstadt (DE); Steven Breakspear, Darmstadt (DE); Bernd Nöcker, Darmstadt (DE); Ines Rabelo De Moraes, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,518

(22) Filed: Feb. 25, 2022

(65) Prior Publication Data

US 2022/0273535 A1 Sep. 1, 2022

(30) Foreign Application Priority Data

Feb. 26, 2021 (EP) ..................... 21159628

(51) Int. Cl.
| | | |
|---|---|---|
| *A61K 8/22* | (2006.01) | |
| *A61K 8/23* | (2006.01) | |
| *A61K 8/25* | (2006.01) | |
| *A61K 8/34* | (2006.01) | |
| *A61K 8/46* | (2006.01) | |
| *A61K 8/60* | (2006.01) | |
| *A61K 8/73* | (2006.01) | |
| *A61Q 5/08* | (2006.01) | |

(52) U.S. Cl.
CPC .................. *A61K 8/22* (2013.01); *A61K 8/23* (2013.01); *A61K 8/25* (2013.01); *A61K 8/342* (2013.01); *A61K 8/463* (2013.01); *A61K 8/60* (2013.01); *A61K 8/731* (2013.01); *A61Q 5/08* (2013.01); *A61K 2800/882* (2013.01)

(58) Field of Classification Search
CPC ... A61K 8/22; A61K 8/23; A61K 8/25; A61K 8/342; A61K 8/463; A61K 8/60; A61K 8/731; A61K 2800/882; A61K 8/345; A61Q 5/08
USPC ........................................................ 424/62
See application file for complete search history.

(56) References Cited

U.S. PATENT DOCUMENTS

| | | |
|---|---|---|
| 5,294,436 A | 3/1994 | Cope et al. |
| 5,344,581 A | 9/1994 | Burzio et al. |
| 2006/0269492 A1* | 11/2006 | Narasimhan ........... A61K 8/585 424/62 |
| 2007/0220684 A1* | 9/2007 | Narasimhan ............. A61Q 5/08 8/405 |
| 2008/0178399 A1* | 7/2008 | Vena ........................ A61Q 5/10 8/407 |
| 2017/0319456 A1* | 11/2017 | Gebert-Schwarzwaelder ............. A61Q 5/065 |

FOREIGN PATENT DOCUMENTS

| | | | |
|---|---|---|---|
| EP | 0 525 239 A1 | 2/1993 | |
| EP | 1671619 A1 * | 6/2006 | ............... A61K 8/19 |
| EP | 3 040 065 A1 | 7/2016 | |
| EP | 2 608 848 B1 | 4/2017 | |
| EP | 3 453 380 A1 | 3/2019 | |
| JP | 61-41367 A | 2/1986 | |
| JP | 2007- 126415 A | 5/2007 | |
| JP | 2008-208120 A | 9/2008 | |
| KR | 2003-0024352 A | 3/2003 | |

OTHER PUBLICATIONS

"Beauté by Roquette PO 260 Polyol—Mannitol." 2019. Knowde, www.knowde.com/stores/roquette/products/beaute-by-roquette-po-260-polyol. (Year: 2019).*
National Center for Biotechnology Information. "PubChem Compound Summary for CID 700, Ethanolamine." 2004. PubChem, https://pubchem.ncbi.nlm.nih.gov/compound/Ethanolamine. Accessed Jun. 15, 2023. (Year: 2004).*
Hoekstra, Steph. "How Do You Measure Color Accuracy?" Nix Sensor Ltd, Apr. 5, 2023, www.nixsensor.com/blog/measure-color-accuracy. (Year: 2023).*
Extended European Search Report issued Sep. 16, 2021 in European Application 21159628.3 filed on Feb. 26, 2021, 9 pages (with Written Opinion).
"Hair Bleaching Agent" , Database GNPD [Online] MINTEL, Oct. 5, 2020, 6 pages, Database accession No. 8158129.
"Decolourant", Database GNPD [Online] MINTEL, Aug. 17, 2016, 5 pages, Database accession No. 4219565.
"Diva Hair Color" , Database GNPD [Online] MINTEL, Oct. 20, 1999, 3 pages, Database accession No. 10062789.
"Ex Hi-Blech Hair Colourant" , Database GNPD [Online] MINTEL, Aug. 20, 2004, 2 pages, Database accession No. 295446.
K. Schrader, Grundlagen und Rezepturen der Kosmetika, 1989, pp. 44-45, 814-823 and 294-297 (with English Summary), 11 pages.
W. Umbach: Kosmetik und Hygiene, 2004, pp. 294-299 (with English Summary), 26 pages.

* cited by examiner

*Primary Examiner* — Benjamin J Packard
*Assistant Examiner* — Lucy M Tien
(74) *Attorney, Agent, or Firm* — Oblon, McClelland, Maier & Neustadt, L.L.P.

(57) ABSTRACT

The present invention is directed to a kit-of-parts for bleaching keratin fibers, having a bleaching composition A comprising a) one or more persalt(s) and/or peroxy salt(s), and b) one or more alkalizing agent(s), an aqueous oxidizing composition B, and a composition C comprising c) one or more non-acetylated sugar alcohol(s), and/or their mixtures, wherein the bleaching composition A comprises less than 5% by weight of water, calculated to the total weight of the bleaching composition A.

9 Claims, No Drawings

BLEACHING COMPOSITION FOR KERATIN FIBERS

CROSS REFERENCES TO RELATED APPLICATIONS

This application claims priority to European Patent Application No. 21159628.3, filed on Feb. 26, 2021, which is incorporated herein by reference in its entirety.

FIELD OF THE INVENTION

The invention is directed to the provision of a kit-of-parts for bleaching of keratin fibers, a ready-to-use composition, and a method for bleaching keratin fibers.

BACKGROUND OF THE INVENTION

Many consumers are unsatisfied with their hair color. Changes of hair color, in most cases, require the lightening of hair, especially for dark hair customers. A common technique is hair bleaching of whole hair as well partial treatments such as streaks. For such treatments a high degree of lightening is desired.

One way to increase lightening performance of bleaching compositions is the use of a reductive pre-treatment step, e.g., by using organic thiols (EP 2 608 848 B1) or inorganic reducing agents such as sulfites. However, with a reductive pre-treatment step hair lightening and hair damage are increased simultaneously.

EP0525239 discloses the use of acetylated sugar alcohols at concentrations of 45 by weight or more to increase the performance of perborate bleach for textile fibers.

EP3040065 discloses the use of mono- and disaccharides in aqueous oxidizing composition.

Thus, there is a real need to develop bleaching composition, which deliver an increased degree of lightening without leading to high degrees of damage.

SUMMARY OF THE INVENTION

The first object of the present invention is a kit-of-parts for bleaching keratin fibers, preferably for human keratin fibers, more preferably for human hair, comprising
  a bleaching composition A comprising
  a) one or more persalt(s) and/or peroxy salt(s), and
  b) one or more alkalizing agent(s),
  an aqueous oxidizing composition B,
  a composition C comprising
  c) one or more non-acetylated sugar alcohol(s), and/or their mixtures,
  wherein the bleaching composition A comprises less than 5% by weight of water, calculated to the total weight of the bleaching composition A, and
  wherein the one or more non-acetylated sugar alcohol(s) of composition C as compound(s) according to group c) is/are mannitol, xylitol, and/or their mixtures.

The second object of the present invention is a ready-to-use bleaching composition having a pH in the range of 7 to 12 comprising
  one or more compound(s) according to group a) as defined above,
  one or more compound(s) according to group b) as defined above,
  one or more oxidizing agent, preferably hydrogen peroxide,
  one or more compound(s) according to group c) as defined above,
  wherein the total concentration of compound(s) according to group c) is in the range of 0.00001% to 1% by weight, calculated to the total weight of the ready-to-use composition.

The pH is measured in this invention with a glass electrode at 25° C. under atmospheric pressure.

The third object of the present invention is a method for bleaching keratin fibers, preferably human keratin fibers, more preferably human hair, comprising the steps of:
  i) mixing a bleaching composition A as defined above with an aqueous oxidizing composition B as defined above, preferably comprising hydrogen peroxide and having a pH in the range of 1 to 6, and a composition C as defined above, to yield a ready-to-use composition having a pH in the range of 7 to 12,
  ii) applying the ready-to-use composition onto keratin fibers and leaving it for a time period of 1 min to 60 min,
  iii) rinsing-off the keratin fibers with water and optionally shampooing the keratin fibers.

DETAILED DESCRIPTION OF THE INVENTION

Inventors of the present invention have unexpectedly found out that a composition according to claim 1 increases bleaching performance while not leading to elevated damage of keratin fibers. Moreover, due to the mildness of the compositions to fibers, they feel more cosmetic, healthier, and appear to have more shine.

Kit-of-Parts

The present invention is directed to a kit-of-parts for bleaching keratin fibers, preferably for human keratin fibers, more preferably for human hair, comprising
  a bleaching composition A comprising
  a) one or more persalt(s) and/or peroxy salt(s), and
  b) one or more alkalizing agent(s),
  an aqueous oxidizing composition B,
  a composition C comprising
  c) one or more non-acetylated sugar alcohol(s), and/or their mixtures,
  wherein the bleaching composition A comprises less than 5% by weight of water, calculated to the total weight of the bleaching composition A, and
  wherein the one or more non-acetylated sugar alcohol(s) of composition C as compound(s) according to group c) is/are mannitol, xylitol, and/or their mixtures.

Bleaching Composition A

The bleaching composition A of the present invention comprises
  a) one or more persalt(s) and/or peroxy salt(s), and
  b) one or more alkalizing agent(s),
  wherein the composition comprises less than 5% by weight of water, calculated to the total weight of the bleaching composition A.

Preferably, the bleaching composition A comprises less than 1% by weight of water, more preferably it is an anhydrous composition, from the viewpoint of stability. The term anhydrous is to be understood that no water is added to the powder. However, this does not exclude any water bound to the ingredients by, for example, capillary forces.

Compound(s) According to Group a)

The bleaching composition A comprises one or more persalt(s) and/or peroxy salt(s) as compound(s) according to group a). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium, and ammonium persulfate.

It is preferred from the viewpoint of bleaching power and cosmetic safety that the total concentration of persalts and/or peroxy salts in the bleach powder composition is in the range of 10% to 80% by weight, preferably 15% to 70% by weight, more preferably 20% to 60% by weight, and still more preferably 25% to 60% by weight, calculated to the total weight of the bleach powder composition.

Compound(s) According to Group b)

The bleaching composition A further comprises one or more alkalizing agent(s) as compounds according to group b). Preferably, the compounds according to group b) are selected from inorganic and/or organic alkalizing agent(s), and/or their mixtures.

It is preferred from the viewpoint of stability and bleaching power that the compounds according to group b) are inorganic alkalizing agent(s), preferably selected from metasilicates, carbonates, and/or bicarbonates, and/or their alkali or earth alkali salts, and/or their mixtures, more preferably the compound according to group b) is sodium metasilicate.

It is preferred from the viewpoint of alkalinity that the compounds according to group b) are organic alkalizing agent(s), preferably selected from alkyl- or alkanolamines according to the general structure

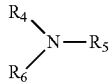

wherein $R_4$, $R_5$, and $R_6$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_4$, $R_5$, or $R_6$ is different from H, and/or their mixtures.

Suitable organic alkalizing agents are monoethanolamine, diethanolamine, triethanolamine, monomethylamine, dimethylamine, trimethylamine, monoethylamine, diethylamine, and 2-aminomethyl propanol.

The most preferred organic alkalizing agent(s) as compounds according to group b) are selected from monoethanolamine and/or 2-aminomethyl propanol.

It is preferred from the viewpoint of alkalinity and stability that the composition comprises one or more compound according to b) at a total concentration in the range of 0.25% to 30% by weight, preferably 0.5% to 25% by weight, more preferably 1% to 20% by weight, calculated to the total weight of the composition.

Optionally, the bleaching composition may comprise one or more ammonium salt(s) different from persalt(s) and peroxy salt(s).

Suitable ammonium salts different from persalt(s) and peroxy salt(s) are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartrate, ammonium benzoate, ammonium acetate, ammonium formate and ammonium lactate. Compositions may also comprise mixtures of ammonium salts.

The bleaching composition A may comprise one or more ammonium salts different from persalt(s) and peroxy salt(s) at a total concentration in the range of 0.1% to 10% by weight, calculated to the total weight of the composition.

Cosmetic Forms of Bleaching Composition A

The bleaching composition A of the present invention may be in the form of a bleaching powder composition.

For preparation of the bleaching powder composition, an excipient may be added. Such an excipient is diatomaceous earth.

It is further preferred from the viewpoint of cosmetic safety that the bleaching powder composition is dust-free. This property can commonly be achieved by adding lipophilic compounds to the bleaching powder. From this viewpoint, the composition comprises one or more lipophilic compound(s) as compound according to group d).

The bleaching composition A may be in the form of a bleaching paste composition. It is further preferred that the bleaching paste comprises one or more lipophilic compound(s) as compound according to group d).

Preferably, the compound according to group d) is selected from $C_{12}$ to $C_{22}$ fatty alcohols, esters of $C_3$ to $C_{12}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

Suitable $C_{12}$ to $C_{22}$ fatty alcohols are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

Suitable hydrocarbon-based products are mineral oil, paraffins, and Vaseline.

Preferred compound(s) according to group d) are alkoxylated organopolysiloxanes from the viewpoint of bleaching power.

Suitable alkoxylated organopolysiloxanes may be alkoxylated aminated or alkoxylated non-aminated organopolysiloxanes.

Suitable alkoxylated aminated organopolysiloxanes are PEG-x amodimethicones where x is an integer ranging from 2 to 100, PEG/PPG-x/y amodimethicones where x/y are in the range of 2 to 100, or mono- or bisalkyl PEG/PPG-x/y amodimethicones with the same denotation for x and y as before.

It is preferred from the viewpoint of dyeing intensity that the alkoxylated non-aminated organopolysiloxane as compound according to d) is an alkoxylated dimethicone copolymer.

Suitable alkoxylated dimethicone copolymers are PEG-x dimethicone where x is an integer ranging from 2 to 100, PEG/PPG-x/y dimethicone where x/y are in the range of 2 to 100, and mono- or bisalkyl PEG/PPG-x/y dimethicones with the same denotation for x and y as before.

Further examples of such compounds are PEG/PPG-14/4 dimethicone; PEG/PPG-4/12 dimethicone; PEG/PPG-23/6 dimethicone; PEG/PPG-20/23 dimethicone; PEG-12 dimethicone and PEG-8 dimethicone, PEG/PPG-3/10 dimethicone; PEG/PPG-4/12 dimethicone; PEG/PPG-6/4 dimethicone; PEG/PPG-6/11 dimethicone; PEG/PPG-8/14 dimethicone; PEG/PPG-8/26 dimethicone; PEG/PPG-10/2 dimethicone; PEG/PPG-12/16 dimethicone; PEG/PPG-12/18 dimethicone; PEG/PPG-14/4 dimethicone; PEG/PPG-15/5 dimethicone; PEG/PPG-15/15 dimethicone; PEG/PPG-16/2 dimethicone; PEG/PPG-16/8 dimethicone; PEG/PPG-17/18 dimethicone; PEG/PPG-18/6 dimethicone; PEG/PPG-18/12 dimethicone; PEG/PPG-18/18 dimethicone; PEG/PPG-19/19 dimethicone; PEG/PPG-20/6 dimethicone; PEG/PPG-20/15 dimethicone; PEG/PPG-20/20 dimethicone; PEG/PPG-20123 dimethicone; PEG/PPG-20129 dimethicone; PEG/PPG-22/23 dimethicone; PEG/PPG-22/24 dimethicone; PEG/PPG-23/6 dimethicone; PEG/PPG-25/25 dimethicone; PEG/PPG-27/27 dimethicone; PEG/PPG-30/10 dimethicone; and/or mixtures thereof.

It is further preferred from the viewpoint of bleaching power that the compound according to d) is selected from ethoxylated dimethicone copolymers, propoxylated dimethicone copolymers, and/or ethoxylated/propoxylated dimethicone copolymers, and/or their mixtures.

The most preferred compound from the viewpoint of bleaching power is PEG/PPG-20/23 dimethicone.

It is preferred from the viewpoint of user convenience that the total concentration of compounds according to d) preferably is 1% by weight or more, more preferably is 5% by weight or more, further more preferably 10% by weight or more, calculated to the total weight of the composition.

It is preferred from the viewpoint of solubility that the total concentration of compounds according to d) preferably is 50% by weight or less, more preferably is 30% by weight or less, further more preferably 20% by weight or less, calculated to the total weight of the bleaching composition A, compositions B and/or C.

For attaining the above-mentioned effects, the total concentration of compounds according to d) is in the range of 1% to 50% by weight, preferably in the range of 5% to 30% by weight, more preferably in the range of 10% to 20% by weight, calculated to the total weight of the bleaching composition A, compositions B and/or C.

It is preferred from the viewpoint of making the composition dust-free or formulating it as a paste that the concentration of compounds according to group d) is in the range of 1% to 20% by weight, preferably 2% to 15% by weight, more preferably 3% to 12% by weight, calculated to the total weight of the bleaching composition A, compositions B and/or C.

Aqueous Oxidizing Composition B

The kit-of-parts of the present invention comprises an aqueous oxidizing composition B.

It is preferred from the viewpoint of stability of the composition, bleaching power, and cosmetic safety that the aqueous oxidizing composition B has a pH of 1 or more, more preferably of 1.5 or more, further more preferably of 2 or more.

It is preferred from the viewpoint of stability of the composition that the pH of the aqueous oxidizing composition B is 6 or less, more preferably 5 or less, further more preferably 4.5 or less.

For attaining the above-mentioned effect, it is preferred that the pH of the aqueous oxidizing composition B is in the range of 1 to 6, preferably in the range of 1.5 to 5, more preferably in the range of 2 to 4.5.

The pH may be adjusted with well-known acids such as phosphoric acid.

It is further preferred from the viewpoint of bleaching power that the aqueous oxidizing composition B comprises hydrogen peroxide as oxidizing agent.

It is preferred from the viewpoint of bleaching power that the total concentration of hydrogen peroxide in the aqueous oxidizing composition B is 1% by weight or more, more preferably 2% by weight or more, further more preferably 3% by weight or more, calculated to the total weight of the aqueous oxidizing composition B.

It is preferred from the viewpoint of cosmetic safety that the total concentration of hydrogen peroxide in the aqueous oxidizing composition B is 20% by weight or less, more preferably 15% by weight or less, further more preferably 12% by weight or less, calculated to the total weight of the aqueous oxidizing composition B.

For attaining the above-mentioned effects, it is preferred that the total concentration of hydrogen peroxide in the aqueous oxidizing composition B is in the range of 1% to 20% by weight, more preferably 2% to 15% by weight, further more preferably 3% to 12% by weight, calculated to the total weight of the aqueous oxidizing composition B.

It is further preferred that the aqueous oxidizing composition B is in the form of an emulsion and optionally comprises one or more lipophilic compound(s) according to d) and/or one or more surfactant(s) according to e).

It is further preferred from the viewpoint of cosmetic safety that the aqueous oxidizing composition B comprises one or more thickening polymer(s).

Composition C

The kit-of-parts of the present invention is also directed to a composition C comprising
  c) one or more non-acetylated sugar alcohol(s), and/or their mixtures, and
  wherein the one or more non-acetylated sugar alcohol(s) of composition C as compound(s) according to group c) is/are mannitol, xylitol, and/or their mixtures.

Compound(s) According to Group c)

The composition C of the present invention comprises mannitol and/or xylitol as one or more non-acetylated sugar alcohol(s), and/or their mixtures, as compound(s) according to group c).

The most preferred non-acetylated sugar alcohol(s) of the composition C as compound(s) according to group c) is mannitol from the viewpoint of bleaching power and commercial availability.

It is preferred from the viewpoint of mixability that the total concentration of compound(s) according to group c), preferably the total concentration of mannitol, in the composition C is 0.001% by weight or more, more preferably 0.0025% by weight or more, further more preferably 0.01% by weight or more, still further more preferably 0.02% by weight or more, calculated to the total weight of the composition C.

It is preferred from the viewpoint of viscosity that the total concentration of compound(s) according to group c), preferably the total concentration of mannitol, in the composition C is 50% by weight or less, more preferably 25% by weight or less, further more preferably 20% by weight or less, still further more preferably 15% by weight or less, still further more preferably 10% by weight or less, still further more preferably 5% by weight or less, calculated to the total weight of the composition C.

For attaining the above-mentioned effects, it is preferred that the total concentration of compound(s) according to group c), preferably the total concentration of mannitol, in the composition C is in the range of 0.001% to 50% by weight, preferably in the range of 0.0025% to 25% by weight, more preferably in the range of 0.01% to 20% by weight, more preferably in the range of 0.02% to 15% by weight, still more preferably in the range of 0.02% to 10% by weight, still further more preferably in the range of 0.02% to 5% by weight, calculated to the total weight of the composition C.

Cosmetic Forms of Composition C

The composition C may be formulated in all suitable cosmetic forms. However, certain forms are preferred.

It is preferred from the ecological viewpoint that composition C is a powder composition.

For preparation of the powder composition, an excipient may be added. Such an excipient, for example, is diatomaceous earth. The powder composition may comprise less than 5% by weight of water, calculated to the total weight of the composition C, and more preferably may be anhydrous.

It is further preferred from the viewpoint of cosmetic safety that the composition C is dust-free. This property can commonly be achieved by adding lipophilic compounds. From this viewpoint, the composition comprises one or more lipophilic compound(s) as compound according to group d).

It is preferred from the viewpoint of user convenience that the composition C is an aqueous composition comprising water at 40% by weight or less, further more preferably comprising water at 30% by weight or less, still further more preferably comprising water at 20% by weight or less, still further more preferably comprising water at 10% by weight or less, still further more preferably comprising water at 5% by weight or less, calculated to the total weight of the composition C.

It is one aspect of the present invention that the composition C is anhydrous.

The composition C, in case it is aqueous, may be in the form of a solution or an emulsion.

For preparation of an emulsion, the composition C optionally comprises one or more lipophilic compound according to d) and/or one or more surfactant(s) according to e).

It is one aspect of the present invention that the composition C is an anhydrous composition being liquid at 25° C. and atmospheric pressure.

The present disclosure is also directed to a composition C comprising:
- c) one or more non-acetylated sugar alcohol(s), and/or their mixtures, as defined above,
- d) one or more alkoxylated organopolysiloxane as compound(s), as defined below
- e) one or more compound(s) selected from alkoxylated glyceryl ester(s) and/or optionally alkoxylated alkyl glyceryl ether(s), and/or their mixtures, at a total concentration of 15% by weight or more, calculated to the total weight of the composition, as defined below, wherein the composition comprises less than 40% by weight of water, calculated to the total weight of the composition.

The present disclosure is also directed to a composition C comprising:
- c) one or more non-acetylated sugar alcohol(s), and/or their mixtures, as defined above,
- d) one or more alkoxylated organopolysiloxane as compound(s), as defined below
- e) one or more compound(s) selected from alkoxylated glyceryl ester(s) and/or optionally alkoxylated alkyl glyceryl ether(s), and/or their mixtures, at a total concentration of 15% by weight or more, calculated to the total weight of the composition, as defined below, wherein the composition C is anhydrous.

Optional Compounds—Surfactants as Compounds According to e)

The bleaching composition A, the aqueous oxidizing composition B, and/or the composition C of the present invention may further comprise one or more surfactant(s) as compound according to group e), preferably selected from non-ionic surfactants, anionic surfactants, cationic surfactants, and/or amphoteric/zwitterionic surfactants, and/or their mixtures, more preferably selected from anionic surfactants and/or non-ionic surfactants, from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures.

Suitable examples are alkyl sulfate or preferably ethoxylated alkyl ether sulfate surfactant or mixtures thereof having an alkyl chain length of $C_{10}$ to $C_{22}$.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants. Suitable examples are cetrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of the bleaching composition A, the aqueous oxidizing composition B, and/or the composition C.

It is particularly preferred for the composition C that it comprises one or more non-ionic surfactant(s) as compound(s) according to e), preferably selected from alkoxylated glyceryl ester(s) and/or optionally alkoxylated alkyl glyceryl ether(s), and/or their mixtures.

It is preferred from the viewpoint bleaching performance that one or more compound according to group e) for the composition C is an ethoxylated and/or propoxylated and/or ethoxylated/propoxylated glyceryl ester with linear or branched, saturated or unsaturated $C_8$ to $C_{22}$ fatty acids, preferably with linear or branched, saturated or unsaturated $C_{14}$ to $C_{22}$ fatty acids.

Suitable compounds are PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid glycerides, PEG-10 olive oil glycerides, PEG-13 sunflower oil glycerides, PEG-7 hydrogenated castor oil, hydrogenated palm kernel oil glyceride PEG-6 ester, PEG-20 corn oil glycerides, PEG-18 glyceryl oleate cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-80 glyceryl cocoate, PEG-60 almond oil glycerides, PEG-60 "evening primrose" glycerides, PEG-200 hydrogenated glyceryl palmate, PEG-90 glyceryl isostearate.

It is preferred from the viewpoint of bleaching performance that that one or more compound according to group e) is PEG-7 glyceryl cocoate, PEG-9 cocoglycerides, PEG-40 hydrogenated castor oil and PEG-200 hydrogenated glyceryl palmate.

It is further preferred from the viewpoint of stability that one or more compound(s) according to group e) is an optionally alkoxylated alkyl glyceryl ether having an unsaturated alkyl chain with a total carbon number of 8 or more, preferably having a total carbon number of 9 or more.

It is preferred from the viewpoint of formulation stability that the alkyl chain of compounds according to group e) is a straight or branched, saturated or unsaturated alkyl chain having a total carbon number of 18 or less.

For attaining the above-mentioned effect, it is preferred that the alkyl chain of compounds according to group e) is a straight or branched, saturated or unsaturated alkyl chain having a total carbon number in the range of 8 to 18, more preferably in the range of 9 to 18.

Suitable examples for compounds according to group e) are isostearyl glyceryl ether, stearyl glyceryl ether, isodecyl glyceryl ether, 2-ethylhexyl glyceryl ether, and cetyl glyceryl ether as well as alkyl polyglyceryl ether as disclosed, for example, in EP2003110.

It is preferred from the viewpoint of stability that the compounds according to group e) are selected from ethoxylated glyceryl cocoate and/or isostearyl glyceryl ether.

It is further preferred from the viewpoint of bleaching performance and formulation stability of the composition C that the total concentration of compounds according to group e) in composition C is 15% by weight or more, further preferably 20% by weight or more, still further preferably 30% by weight or more, calculated to the total weight of the composition C.

It is preferred from the viewpoint of solubility of the composition C that the total concentration of compounds according to group e) in composition C is 80% by weight or less, further preferably 70% by weight or less, still further preferably 65% by weight or less, calculated to the total weight of the composition C.

For attaining the above-mentioned effects, it is preferred that the total concentration of compounds according to group e) in composition C is in the range of 15% to 80% by weight, preferably in the range of 20% to 70% by weight, more preferably in the range of 30% to 65% by weight, calculated to the total weight of the composition C.

Optional Compounds—Thickening Polymers

In case the viscosity after mixing with other compositions needs to be further adjusted to prevent dripping, the bleaching composition A, the aqueous oxidizing composition B, and/or the composition C may comprise one or more thickening polymers, from the viewpoint of cosmetic safety.

The composition of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 7 and 12 having a viscosity of at least 1,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as $(C_2-C_8)$-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch-based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers in compositions A, B, and/or C are 0.1% by weight or more, more preferably 0.25% by weight or more, more preferably 0.5% by weight or more, calculated to the total weight of the compositions A, B, and/or C, from the viewpoint of providing sufficient viscosity to the ready-to-use composition.

Preferably, the total concentration of thickening polymers compositions A, B, and/or C are 15% by weight or less, more preferably 12% by weight or more, further more preferably 10% by weight or less, calculated to the total weight of the compositions A, B, and/or C, from the viewpoint of providing sufficient viscosity to the composition and cost of goods.

For attaining the above-mentioned effects, it is preferred that the total concentration of thickening polymers compositions A, B, and/or C is in the range of 0.1% to 15% by weight, preferably 0.25% to 12% by weight, more preferably in the range of 0.5% to 10% by weight, calculated to the total weight of the compositions A, B, and/or C.

Ready-to-Use Composition

The present invention is also directed to a ready-to-use bleaching composition having a pH in the range of 7 to 12 comprising
  one or more compound(s) according to group a) as defined above,
  one or more compound(s) according to group b) as defined above,
  one or more oxidizing agent, preferably hydrogen peroxide,
  one or more compound(s) according to group c) as defined above,
  wherein the total concentration of compound(s) according to group c) is in the range of 0.00001% to 1% by weight, calculated to the total weight of the ready-to-use composition.

More preferably, from the viewpoint of bleaching performance, the total concentration of compound(s) according to group c) is in the range of 0.00002% to 0.5% by weight, still more preferably in the range of 0.00002% to 0.25% by weight, still more preferably in the range of 0.00002% to 0.05% by weight, calculated to the total weight of the ready-to-use composition.

Method for Bleaching

The present invention is also directed to a method for bleaching keratin fibers, preferably human keratin fibers, more preferably human hair, comprising the steps of:
  i) mixing a bleaching composition A as defined above with an aqueous oxidizing composition B as defined above, preferably comprising hydrogen peroxide and having a pH in the range of 1 to 6, and a composition C as defined above, to yield a ready-to-use composition having a pH in the range of 7 to 12,
  ii) applying the ready-to-use composition onto keratin fibers and leaving it for a time period of 1 min to 60 min,
  iii) rinsing-off the keratin fibers with water and optionally shampooing the keratin fibers.

The bleaching composition A is mixed with the aqueous oxidizing composition B and composition C to form a ready-to-use composition. Suitable mixing ratios by weight are 5:1:0.01 to 1:5:0.5 (bleach powder composition A:aqueous oxidizing composition B:composition C). Customarily, suitable mixing ratios are 1:1:0.04, 1:1.4:0.02, 1:2:0.5, and 1:3:0.5 by weight (bleaching composition A:aqueous oxidizing composition B:composition C).

Suitably, the pH of the ready-to-use composition is in the range of 7 to 12. It is preferred from the viewpoint of accelerated bleaching that the pH of the ready-to-use composition is in the range of 7.5 to 11, more preferably 8.0 to 10.5.

The ready-to-use composition is then applied to keratin fibers and left for a time period of 1 min to 60 min as defined in step ii). Preferred time ranges for step ii) are 5 min to 45 min, more preferred ranges are 10 min to 35 min, from the viewpoint of sufficiently bleaching the keratin fibers.

After that, the ready-to-use composition is rinsed-off from keratin fibers and optionally they are shampooed and optionally blow-dried.

The following examples are to illustrate the invention, but not to limit it.

EXAMPLES

The following compositions were prepared:

| Bleaching composition A | |
|---|---|
| | % by weight |
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| Mineral oil | 8 |
| Diatomaceous Earth | to 100 |

| Aqueous oxidizing composition B | |
|---|---|
| | % by weight |
| Cetearyl alcohol | 4.0 |
| Sodium lauryl sulfate | 0.8 |
| Phosphoric acid | q.s. ad pH 2.5 |
| Tetrasodium EDTA | 0.05 |
| Hydrogen peroxide | 6.0 |
| Water | ad 100.0 |

| | Composition C | | | | | |
|---|---|---|---|---|---|---|
| Ingredient | Inv. ex. 1 | Inv. ex. 2 | Inv. ex. 3 | Inv. ex. 4 | Comp. ex. 1 | Comp. ex. 2 |
| | % by weight | | | | | |
| Mannitol | 2.5 | 0.25 | 0.025 | 0.0025 | — | — |
| Sorbitol | — | — | — | — | — | 2.5 |
| Water | | | | Ad 100.0 | | |
| Final sugar alcohol concentration in ready-to-use mixture | 0.02 | 0.002 | 0.0002 | 0.00002 | — | 0.02 |
| L* | 40.73 | 41.06 | 39.69 | 39.39 | 36.73 | 36.67 |
| a* | 11.88 | 11.48 | 12.04 | 11.66 | 11.48 | 12.14 |
| b* | 25.84 | 26.00 | 25.53 | 24.92 | 22.86 | 23.74 |
| ΔE | 49.68 | 49.94 | 48.70 | 48.05 | 44.76 | 45.34 |

Evaluation

The inventive compositions comprising mannitol exhibited a higher ΔE value in all cases in comparison to comparative composition 1 not comprising sugar alcohols and comparative composition 2 comprising sorbitol. Thus, the bleaching performance was increased by using the inventive compositions.

Methods

Bleaching Method

Caucasian hair streaks (21 cm, 2 g per bundle) were purchased from Fischbach+Miller Haar, Laupheim, Germany. The bleaching composition A, aqueous oxidizing composition B, and composition C from above were mixed in a weight ratio of 1:1.4:0.02 (bleaching composition A:aqueous oxidizing composition B:composition C) to prepare a ready-to-use composition with a pH of 10.0±0.2. 5 g of the ready-to-use compositions were applied onto hair streaks and left for 30 min at room temperature. The hair streaks were then rinsed-off with lukewarm water, shampooed with a shampoo commercially available under the trade name Goldwell Deep Cleansing Shampoo, and blow-dried.

Lightening Measurements

L*, a*, b* values were measured before (L*o, a*o, b*o) and after bleaching (L*i, a*$_1$, b*i) with a Datacolor 45G instrument.

ΔE was calculated by the following equations:

$$\Delta E = \sqrt{(L_1^* - L_0^*)^2 + (a_1^* - a_0^*)^2 + (b_1^* - b_0^*)^2}$$

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The following examples are within the scope of the present invention.

Example 5

| Composition C | % by weight |
| --- | --- |
| Mannitol | 10.0 |
| Cetearyl alcohol | 5.0 |
| PEG-7 glyceryl cocoate | 30.0 |
| NaOH/HCl | ad pH 7 |
| Water | ad 100.0 |

Example 6

| Composition C | % by weight |
| --- | --- |
| Mannitol | 10.0 |
| Mineral oil | 2.0 |
| PEG-7 glyceryl cocoate | 30.0 |
| Diatomaceous earth | ad 100.0 |

The invention claimed is:

1. A kit-of-parts for bleaching keratin fibers, comprising a bleaching composition A comprising
   a) one or more persalt(s) and/or peroxy salt(s) at a total concentration in the range of 20% to 80% by weight, calculated to the total weight of the bleaching composition A, and
   b) one or more alkalizing agent(s) selected from metasilicates, carbonates, bicarbonates, and/or their alkali or earth alkali salts, at a total concentration in the range of 1% to 20% by weight, calculated to the total weight of the bleaching composition A;

an aqueous oxidizing composition B having a pH in a range of 1 to 6 and comprising hydrogen peroxide; and a composition C comprising
   c) mannitol, at a total concentration in the range of 0.001% to 5% by weight, calculated to the total weight of the composition C, wherein the bleaching composition A comprises less than 5% by weight of water, calculated to the total weight of the bleaching composition A, wherein a total concentration of mannitol in a ready-to-use mixture obtained by mixing the bleaching composition A, the aqueous oxidizing composition B, and the composition C, is in the range of 0.00002% to 0.05% by weight, calculated to the total weight of the ready-to-use mixture.

2. The kit-of-parts according to claim 1, wherein the total concentration of mannitol e) in the composition C is in the range of 0.02% to 5% by weight, calculated to the total weight of the composition C.

3. The kit-of-parts according to claim 1, wherein the composition C is a powder composition.

4. The kit-of-parts according to claim 1, wherein composition C is an aqueous composition comprising water at 40% by weight or less, calculated to the total weight of composition C, or the composition C is an anhydrous composition.

5. The kit-of-parts according to claim 1, wherein composition C is an aqueous composition comprising water at 10% by weight or less, calculated to the total weight of composition C.

6. The kit-of-parts according to claim 1, wherein the bleaching composition A and/or composition C comprise(s) one or more lipophilic compound(s) as compound(s) selected from C12 to C22 fatty alcohols, esters of C3 to C12 alcohols with C12 to C22 fatty acids, C8 to C22 fatty acids, vegetable oils, silicones, hydrocarbon products, and/or their mixtures.

7. The kit-of-parts according to claim 1 wherein composition C further comprises one or more non-ionic surfactant(s) selected from alkyl polyglycosides, ethoxylated triglycerides, ethoxylated fatty alcohols, ethoxylated fatty acid esters, and/or their mixtures.

8. A ready-to-use bleaching composition having a pH in the range of 7 to 12 comprising
   a) one or more persalt(s) and/or peroxy salt(s),
   b) one or more alkalizing agent(s) selected from metasilicates, carbonates, bicarbonates, and/or their alkali or earth alkali salts,
   hydrogen peroxide, and
   c) mannitol,
   wherein the total concentration of mannitol e) is in the range of 0.00002% to 0.05% by weight, calculated to the total weight of the ready-to-use composition.

9. A method for bleaching keratin fibers using the kit-of-parts according to claim 1, the method comprising:
   i) mixing a bleaching composition A as defined in claim 1 with an aqueous oxidizing composition B as defined in claim 1, and a composition C as defined in claim 1 to yield a ready-to-use composition having a pH in the range of 7 to 12,
   ii) applying the ready-to-use composition onto keratin fibers and leaving it for a time period of 1 min to 60 min, and
   iii) rinsing-off the keratin fibers with water and optionally shampooing the keratin fibers.

* * * * *